United States Patent [19]

Tschunt

[11] 4,347,624
[45] Aug. 31, 1982

[54] X-RAY DIAGNOSTIC APPARATUS FOR PRODUCING TRANSVERSE LAYER IMAGES

[75] Inventor: Edgar Tschunt, Rathsberg, Fed. Rep. of Germany

[73] Assignee: Siemens Aktiengesellschaft, Berlin & Munich, Fed. Rep. of Germany

[21] Appl. No.: 115,751

[22] Filed: Jan. 28, 1980

Related U.S. Application Data

[62] Division of Ser. No. 875,385, Feb. 6, 1978, Pat. No. 4,219,733.

[30] Foreign Application Priority Data

Apr. 1, 1977 [DE] Fed. Rep. of Germany ....... 2714759

[51] Int. Cl.³ .............................................. G03B 41/16
[52] U.S. Cl. ......................................... 378/10; 378/9; 378/19
[58] Field of Search ............................ 250/445 T, 360

[56] References Cited

U.S. PATENT DOCUMENTS

| | | | |
|---|---|---|---|
| 4,137,455 | 1/1979 | Fetter | 250/445 T |
| 4,153,842 | 5/1979 | Rohmfeld | 250/360 |
| 4,203,036 | 5/1980 | Tschunt | 250/445 T |
| 4,206,362 | 6/1980 | Bagby | 250/445 T |

Primary Examiner—Alfred E. Smith
Assistant Examiner—Carolyn E. Fields
Attorney, Agent, or Firm—Hill, Van Santen, Steadman, Chiara & Simpson

[57] ABSTRACT

In an illustrated embodiment, the fan-shaped x-ray beam is rotated by electronic switching and a detector ring is gimbaled so that only the desired sector thereof intercepts the beam. A collimator ring may be rotated in step with the beam and have a pin and slot coupling with the detector ring to control the swiveling thereof.

8 Claims, 4 Drawing Figures

X-RAY DIAGNOSTIC APPARATUS FOR PRODUCING TRANSVERSE LAYER IMAGES

This is a division of application Ser. No. 875,385, filed Feb. 6, 1978, now U.S. Pat. No. 4,219,733.

BACKGROUND OF THE INVENTION

The invention relates to an x-ray diagnostic apparatus for producing transverse layer images of a radiography subject with an x-ray measuring arrangement comprising an x-ray source which produces a fan-shaped beam of x-rays penetrating the radiography subject, the cross-sectional extent of the beam perpendicular to the layer plane being equal to the layer thickness and in the layer plane being of a magnitude such that the whole layer is penetrated with radiation, and comprising also a radiation receiver which ascertains the transmitted radiation intensity, said radiation receiver being constructed as a circular ring into which the radiography subject may be inserted and consisting of a series of detectors, and with means for changing the direction of the x-ray beam's axis of symmetry, and with a computer for the transformation of the signals supplied by the radiation receiver into a layer image.

Described in U.S. Pat. No. 3,778,614 is an x-ray diagnostic apparatus which has all these features apart from the circular radiation receiver. In this known x-ray diagnostic apparatus, the radiation receiver is laterally displaceable. When the subject is scanned, lateral displacement movements and rotational movements through a prescribed angle, e.g. 1°, follow one another alternately until the entire subject is scanned. From the measured absorption values the computer calculates the transverse layer image in the form of a matrix of image point data. The drawback with this x-ray diagnostic apparatus is that, because of the necessary mechanical movement of the radiation receiver and the x-ray tube, the time required for an image exposure is relatively long.

In the publication "Computerized Tomographic Scanner" issued by American Science and Engineering, Inc., publication number ASE-3869, an x-ray diagnostic apparatus of the type stated at the beginning is described. This x-ray diagnostic apparatus thus has a circular radiation receiver which encloses the radiography subject. All that is necessary is a rotational movement of the x-ray source disposed inside the radiation receiver, but no movement of the radiation receiver. The time required for an image exposure is therefore reduced relative to the apparatus known through U.S. Pat. No. 3,778,614. Furthermore, a simpler mechanical structure also results.

SUMMARY OF THE INVENTION

The object underlying the invention is to improve still further an x-ray diagnostic apparatus of the type specified at the beginning with respect to the image exposure time required. The purpose of the invention, in particular, is to create an apparatus of a type in which the mechanical movements are reduced to a minimum.

According to the invention, this object is achieved by virtue of the fact that the x-ray source comprises a hollow evacuated glass ring arrangement, concentrically encircling the radiation receiver, in which hollow ring arrangement a circular anode arrangement is disposed and opposite said anode arrangement a number of cathodes are disposed, the number being dependent on the desired measured value number, that there are means present for the step-by-step actuation of the electron radiation between at least one cathode, respectively, and the anode arrangement, that the radiation receiver is mounted on gimbals and that it is acted upon by guide means which are so designed that they swivel into the x-ray beam the particular part of the radiation-receiver which is required for detecting the x-radiation issuing from the radiography subject. In the case of the x-ray diagnostic apparatus according to the invention, a rotational movement of the x-ray beam is effected in a purely electronic manner by step-by-step successive releasing of the electron radiation between one cathode, respectively, and the anode. Since the x-ray source encircles the radiation receiver coaxially, the gimbal mounting of the radiation receiver and its turning movement ensures that the incident x-ray beam bypasses laterally past the radiation receiver and only impinges on it after it has penetrated the radiography subject. A minimum of mechanical movements is sufficient for the apparatus according to the invention to effect a scan of the radiography subject. The exposure time can therefore be very short.

Within the scope of the invention, a collimator can be mounted within the radiation receiver capable of rotation about the axis of the x-ray source and the radiation receiver, the lamellae of which are aligned with the rays from the x-ray source and which is connected to the radiation receiver by pins guided in a groove. In this way, the pivoting movement of the radiation receiver takes place automatically as the collimator rotates.

The invention is explained in more detail below with reference to an embodiment represented in the accompanying sheets of drawings; other objects, features and advantages will be apparent from this detailed disclosure and from the appended claims.

DETAILED DESCRIPTION

Figure 1:
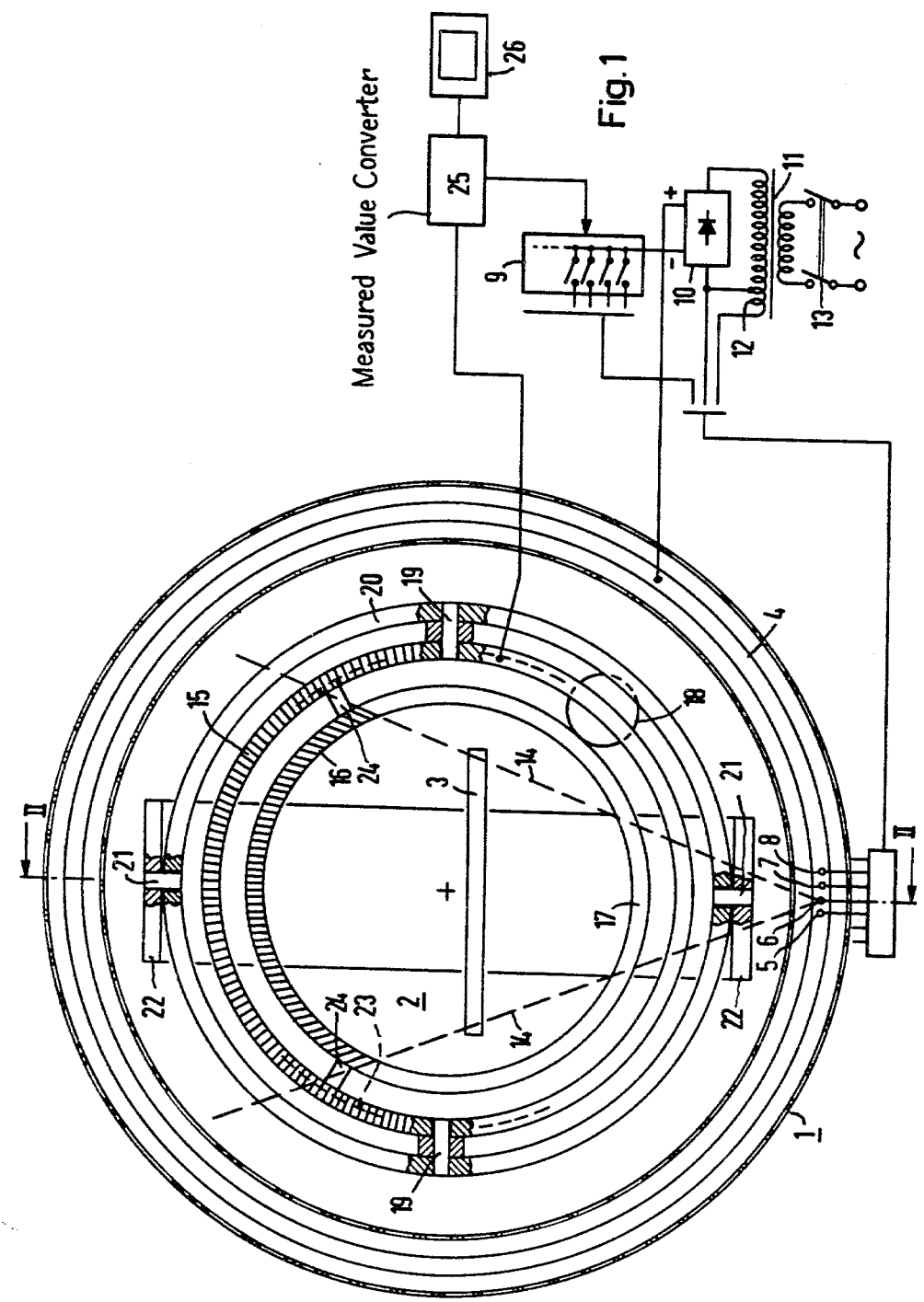
FIG. 1 is a diagrammatic vertical sectional view of an x-ray diagnostic apparatus according to the invention.
Figure 2:
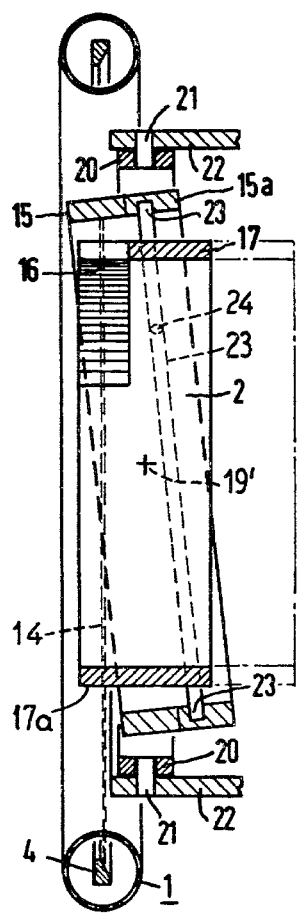
FIG. 2 shows a diagrammatic longitudinal sectional view taken generally as indicated by the line II—II in FIG. 1.
Figure 3:
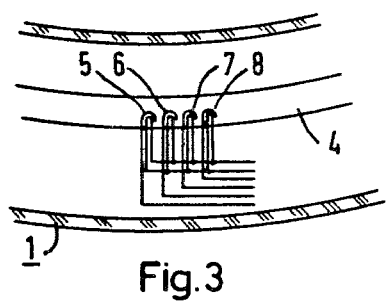
FIGS. 3 and 4 show details of the apparatus according to FIGS. 1 and 2.

The apparatus according to FIGS. 1 and 2 has an x-ray source 1, designed as an evacuated hollow glass ring or tube, which encircles a concentric opening 2. In the opening 2, a patient is supported on a couch 3 which is not represented in FIG. 2 for the sake of clarity. According to FIG. 3 the x-ray tube 1 contains a circular anode 4 with which a plurality of cathodes 5 to 8 etc. are associated. The cathodes 5 to 8 etc. are all preheated via appropriate heating coils during an exposure and shortly before an exposure. The production of the x-radiation, issuing from the anode 4, at a particular point proceeds by connecting one of the cathodes 5 to 8 etc., respectively, via a switching device 9, to the negative pole of a high voltage rectifier 10. The positive pole of the high voltage rectifier 10 is connected to the anode 4. The high voltage rectifier 10 is supplied by a high voltage transformer 11 which, on its secondary side, has a heating winding 12 which effects the heating of the heating coils of the cathodes 5 to 8 etc. The primary winding of the high voltage transformer 11 is connectable to the power supply via a main switch 13.

Figure 4:
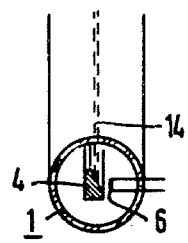

The shape of the anode 4 in cross-section is revealed clearly from FIG. 4. The x-radiation issues from it as a fan-shaped beam 14, the direction of which is dependent on the particular cathode 5 to 8 etc., which is actuated by means of the switching device 9. The structural parts, particularly the x-ray tube 1, are not drawn to scale in the figures.

In the sample embodiment, the x-ray beam 14 is emitted straight (radially inwardly) from the anode 4. To examine a patient lying on the couch 3, the cathodes 5 to 8 etc. and further cathodes extending along the entire anode 4, are actuated progressively (in step-by-step fashion), so that the direction of the x-ray beam 14 changes progressively. The x-ray beam is thus rotated progressively in a clockwise or a counter-clockwise direction. In practice, an expedient method is to provide 360 cathodes, for example, and to rotate the x-ray beam 14 by one degree each time, so that, after a complete rotation movement has been completed, the beam has been rotated through 360 degrees.

The x-ray beam 14 issuing from the patent lying on the couch 3 is detected by a circular radiation receiver 15 consisting of a series of individual detectors. The number of individual detectors is selected according to the desired image resolution. Impingement is always on a number of individual detectors corresponding to the angle of aperture of the fan-shaped x-ray beam. The detectors which are impinged upon in each instance depends on the particular cathode activated at the time. The radiation receiver 15 is not rotated while the patient is being scanned; during scanning the x-ray beam 14 is rotated round the patient by means of sequence switch 9.

Situated in front of the x-ray receiver 15, viewed in radiation direction, is a collimator 16 whose lamellae are aligned with the active focus of the anode 4 of the x-ray source 1. The collimator 16 is attached to a ring 17 which is rotated by a drive device 18, while a patient is being scanned, such that the lamellae of the collimator 16 are always aligned with the particular active focus of the x-ray tube 1.

In the case of the x-ray apparatus according to FIGS. 1 to 4, it is ensured that the x-ray beam 14 first runs laterally past the radiation receiver 15, then penetrates a radiation-permeable part 17a of the ring 17 and subsequently the patient and the collimator 16. Thereafter, the x-ray beam 14 impinges on the radiation receiver 15. This is clear from FIG. 2. FIGS. 1 and 2 show that in order to achieve this objective, the radiation receiver 15 is mounted on a carrier ring 20 by means of two bearings 19, FIG. 1, with the ability to swivel about a horizontal axis (indicated at 19', FIG. 2), and that the carrier ring 20 is mounted in two bearing brackets 22 carrying two bearings 21 which provide for swiveling of the carrier ring 20 about a vertical axis. The radiation receiver 15 is thus mounted on gimbals and is universally pivotable. A ring 15a bearing the receiver 15 has a circular groove 23 on its inside which is particularly visible in FIG. 2. In the groove 23, two pins 24 (FIG. 1) are guided by means of roller bearings disposed at the ends of pins 24 and engaging one of the side walls of the groove 23, the pins 24 being fixed to the collimator ring 17. The pins 24 have the effect that only that part of the radiation receiver 15, which is required for detecting the x-radiation issuing from the radiography subject is swivelled into the x-ray beam 14. All other parts of the radiation receiver 15 lie outside the x-ray beam 14.

When the x-ray beam 14 is rotated, the collimator ring 17 with the collimator 16 is correspondingly rotated at the same time and thus causes the radiation receiver 15 to swivel in the manner illustrated via the pins 24 guided in the groove 23. The mechanical movements are restricted to a minimum in the x-ray apparatus described. There is merely a slight swivelling movement of the radiation receiver 15 and simple circular rotation of the relatively light collimator ring 17.

It is also clear from FIG. 1 that the radiation receiver 15 is connected to a measured value converter or computer 25 which calculates from the output signals of the individual detectors of the radiation receiver 15 the attenuation values of predetermined points of the irradiated layer of the patient in the form of a matrix and effects the reproduction of the image of this layer on a video device 26. The computer 25 controls the switching device 9 for the step-by-step actuation of cathodes 5 to 8 etc. It is also clear from FIGS. 1 and 2 that the x-ray beam 14 penetrates the patient completely in the transverse layer to be examined and that, perpendicularly to this layer, it has an extent which is equal to the thickness of this layer.

Within the scope of the invention the x-ray source need not have a single glass ring or toroidal envelope accommodating the anode and the cathodes. It is also possible to construct the x-ray source from tubular ring segments.

As shown in FIG. 1, for each position of the x-ray beam 14, the collimator 16 has a corresponding position with the laminellae thereof aligned with respective rays of the x-ray beam from the active focus. The arcuate extent of the beam 14, FIG. 1, corresponds to the active extent of the collimator 16, the guide pins 24 being located at the margins of the beam 14 and having an angular separation generally corresponding to the arcuate width of the beam 14 where it impinges on the radiation receiver 15.

Reference is made to my copending application Ser. No. 817,209 filed July 20, 1977, now U.S. Pat. No. 4,203,036, and the disclosure of said copending application is incorporated herein by reference.

In the embodiment illustrated in the present drawings, the plane of the fan-shaped beam 14 corresponds to the radial plane of the focii (beam origin points) of anode 4 as indicated in FIG. 4, the axis of symmetry of the beam 14 being directed radially of anode 4.

It will be apparent that many modifications and variations may be effected without departing from the scope of the novel concepts and teachings of the present invention.

I claim as my invention:

1. An x-ray diagnostic apparatus for producing transverse layer images of a radiography subject with an x-ray measuring arrangement comprising an x-ray source which produces a fan-shaped x-ray beam penetrating the radiography subject, the cross-sectional extent of the beam, perpendicular to the layer plane, being equal to the layer thickness and, in the layer plane, being of such a magnitude that the entire layer is penetrated with radiation, and comprising also a radiation receiver which detects the intensity of radiation emanating from the layer, said radiation receiver being constructed as a circular ring into which the radiography subject may be inserted and comprising a series of detectors, with means for changing the direction of the axis of symmetry of the x-ray beam to effect a scanning operation, and with a measured value converter for the transformation of the signals supplied by the radiation receiver during a scanning operation into a layer image, characterized in that the x-ray source (1) is arranged outside the radiation receiver (15), in that the radiation receiver (15) has gimbal mounting means, and guide means (24) acting on said radiation receiver (15) for swiveling that particular part of the circular ring forming the radiation receiver (15), which is required to detect the x-radiation issuing from the radiography subject, into the x-ray beam (14).

2. An x-ray diagnostic apparatus for producing transverse layer images of a radiography subject with an x-ray measuring arrangement comprising an x-ray source which produces a fan-shaped x-ray beam penetrating the radiography subject, the cross-sectional extent of the beam, perpendicular to the layer plane, being equal to the layer thickness and, in the layer plane, being of such a magnitude that the entire layer is penetrated with radiation, and comprising also a radiation receiver which detects the intensity of radiation emanating from the layer, said radiation receiver being constructed as a circular ring into which the radiography subject may be inserted and comprising a series of detectors, with means for shifting the instantaneous origin point of the x-ray beam and for simultaneously changing the direction of the axis of symmetry of the x-ray beam to effect a scanning operation, and with a measured value converter for the transformation of the signals supplied by the radiation receiver during a scanning operation into a layer image, characterized in that the x-ray source (1) provides an instantaneous origin point for the x-ray beam (14) for each direction of the axis of symmetry thereof which is outside of the circular ring forming said radiation receiver (15), the radiation receiver (15) having mounting means (19-22) accommodating shifting movement of the circular ring forming said radiation receiver (15) such that for each direction of the axis of symmetry of the x-ray beam (14) the part of the circular ring which is adjacent the instantaneous origin point for such x-ray beam (14) is laterally offset from such x-ray beam, and guide means (24) for positioning said circular ring forming said radiation receiver (15) such that for each instantaneous origin point the adjacent part of the circular ring is laterally offset from the x-ray beam (14) while the part of the circular ring required to detect x-radiation issuing from the radiography subject is disposed in the path of the x-ray beam (14) from such instantaneous origin point.

3. Apparatus according to claim 2, characterized in that, inside the radiation receiver (15), a collimator (16) is rotatably mounted about a central axis, the collimator (16) having lamellae which are aligned with ray paths from the instantaneous origin point of the x-ray source (1), and the collimator (16) and the radiation receiver (15) having said guide means acting therebetween in the form of a pin (24) and groove (23) coupling.

4. Apparatus according to claim 3, characterized in that the circular ring forming the radiation receiver (15) carries the groove (23) of said pin and groove coupling, said coupling further comprising pins (24) disposed in arcuately spaced relation on the collimator (16) and having an arcuate separation generally corresponding to the arcuate width of the x-ray beam (14, FIG. 1) impinging on the radiation receiver (15).

5. X-ray diagnostic apparatus for the examination of a transverse layer of a radiography subject, comprising (a) x-ray source means for producing respective fan-shaped x-ray beams (14) penetrating the radiography subject from respective different directions, with origin points of the respective fan-shaped beams being equidistant from a central axis, the cross-sectional extent of the beams, perpendicular to the layer plane, being equal to the layer thickness, and the lateral extent of the beams in the layer plane corresponding to the lateral extent of the layer to be examined so that the entire layer is penetrated with radiation upon production of each beam, (b) patient support means (3) for locating a radiography subject such that the fan-shaped x-ray beams are directed from the x-ray source means toward the layer to be examined from the respective different directions, and such that the central axis intersects the layer to be examined, (c) scanning means for effecting irradiation of the layer to be examined from respective different directions to produce respective scans thereof and operable for effecting a rotational displacement of the direction from which the layer is scanned by sequentially producing fan-shaped x-ray beams (14) from the x-ray source means which are directed toward the layer from successive angularly offset positions about said central axis, and operable during a scanning operation for producing a sufficient number of scans of the layer to be examined so as to enable production of an image thereof, (d) detector means comprising a series of detectors, sensitive to said radiation, disposed at successive positions about the patient support means and arranged such that radiation of each of the fan-shaped beams will impinge on a plurality of successive detectors of said series without requiring rotational movement of said detectors in the direction of rotational displacement of said scanning means during a scanning operation of said scanning means, (e) said detectors of said series being substantially immobile in the direction of rotational displacement of the scanning means throughout a scanning operation of said scanning means, (f) means for locating said detectors so that the distance of each detector from said central axis is less than the distance of the origin points of the fan-shaped beams from the central axis during a scanning operation of said scanning means, and (g) means for moving potentially beam obstructing detectors of said series for the time being disposed at the same side of the central axis as an origin point of a fan-shaped beam to be produced so that such detectors do not obstruct the detection of radiation from such origin point by detectors of said series disposed on the side of the central axis opposite to that of such origin point.

6. X-ray diagnostic apparatus according to claim 5, with said detector means comprising a circular radiation receiver (15) having said series of detectors disposed at successive positions therealong, said means for moving potentially beam obstructing detectors of said series being arranged for moving said circular radiation receiver (15) as a unit.

7. X-ray diagnostic apparatus according to claim 6, with said means for moving comprising a ring rotatable about said central axis during a scanning operation and coupled with said radiation receiver to maintain the axis of the radiation receiver inclined to said central axis such that potentially beam obstructing detectors of said series are offset from each sequentially produced fan-shaped x-ray beam.

8. X-ray diagnostic apparatus for the examination of a transverse layer of a radiography subject, comprising
(a) x-ray source means for producing respective fan-shaped x-ray beams (14) penetrating the radiography subject from respective different directions, with origin points of the respective fan-shaped beams being equidistant from a central axis, the cross-sectional extent of the beams, perpendicular to the layer plane, being equal to the layer thickness, and the lateral extent of the beams in the layer plane corresponding to the lateral extent of the layer to be examined so that the entire layer is penetrated with radiation upon production of each beam,
(b) patient support means (3) for locating a radiography subject such that the fan-shaped x-ray beams are directed from the x-ray source means toward the layer to be examined from the respective different directions, and such that the central axis intersects the layer to be examined,
(c) scanning means for effecting irradiation of the layer to be examined from respective different directions to produce respective scans thereof and operable for effecting a rotational displacement of the direction from which the layer is scanned by sequentially producing fan-shaped x-ray beams (14) from the x-ray source means which are directed toward the layer from successive angularly offset positions about said central axis, and operable during a scanning operation for producing a sufficient number of scans of the layer to be examined so as to enable production of an image thereof,
(d) detector means comprising a series of detectors, sensitive to said radiation, disposed at successive positions so as to completely encircle the patient support means and arranged such that radiation of each of the fan-shaped beams will impinge on a plurality of successive detectors of said series without requiring rotational movement of said detectors in the direction of rotational displacement of the scanning means during a scanning operation of said scanning means,
(e) said detectors of said series being substantially immobile in the direction of rotational displacement of the scanning means throughout a scanning operation of said scanning means,
(f) means for locating said detectors so that the distance of each detector from said central axis is less than the distance of the origin points of the fan-shaped beams from the central axis during a scanning operation of said scanning means, said detectors of said series including with respect to each origin point, an adjacent series of detectors located on the same side of the central axis as such origin point, and a remote series of detectors located on the opposite side of the central axis from such origin point, and
(g) means constructed so as to laterally offset, with respect to each origin point, the adjacent series of detectors relative to the fan-shaped x-ray beam therefrom, so that the fan-shaped beam from each origin point impinges on the radiography subject without obstruction by such adjacent series of detectors, and so as to position the remote series of detectors with respect to each origin point so that the fan-shaped beam from each origin point impinges on such remote series of detectors.

* * * * *

Notice of Adverse Decision in Interference

In Interference No. 101,228, involving Patent No. 4,347,624, E. Tschunt, X-RAY DIAGNOSTIC APPARATUS FOR PRODUCING TRANSVERSE LAYER IMAGES, final judgment adverse to the patentee was rendered Nov. 30, 1989, as to claims 2, 5-8.

*( Official Gazette May 8, 1990 )*